United States Patent
Bichler et al.

(10) Patent No.: US 10,022,095 B2
(45) Date of Patent: Jul. 17, 2018

(54) SUPPORT STRUCTURE WITH RAISABLE COVER

(71) Applicant: General Electric Company, Schenectady, NY (US)

(72) Inventors: Benjamin Bichler, Milwaukee, WI (US); Timothy Behlmer, Milwaukee, WI (US); Kenwood Dayton, Mequon, WI (US); Brandon Smith, Waukesha, WI (US); Ronald Kulas, Delafield, WI (US); John Gilmore, Wauwatosa, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 122 days.

(21) Appl. No.: 14/943,562

(22) Filed: Nov. 17, 2015

(65) Prior Publication Data

US 2017/0135657 A1 May 18, 2017

(51) Int. Cl.
*E05F 15/00* (2015.01)
*A61B 6/00* (2006.01)
*A61B 6/03* (2006.01)
*A61B 6/04* (2006.01)

(52) U.S. Cl.
CPC ............ *A61B 6/4435* (2013.01); *A61B 6/032* (2013.01); *A61B 6/0407* (2013.01)

(58) Field of Classification Search
CPC ....... A61B 6/4447; A61B 6/032; A61B 6/035; A61B 6/4405; A61B 6/04; A61B 6/508; E05Y 2201/434; E05F 15/53; E05F 15/63; E05F 1/1091
USPC .................................. 378/4, 19, 210; 49/136
See application file for complete search history.

(56) References Cited

U.S. PATENT DOCUMENTS

| 4,609,216 A | 9/1986 | Baker et al. |
| 2008/0078123 A1* | 4/2008 | Wei ........................ A61B 6/035 49/136 |

FOREIGN PATENT DOCUMENTS

CN   103371845 A   10/2013

* cited by examiner

*Primary Examiner* — Don Wong
(74) *Attorney, Agent, or Firm* — Fletcher Yoder, P.C.

(57) ABSTRACT

A support structure is disclosed. The support structure has at least one cover installed to cover a side of the support structure. The cover is raised pivotally by at least one primary support mechanism. The cover may be secured in place by an additional support mechanism. The additional support mechanism may be set in two different positions, one that allows for load on the primary support mechanism and another that does not allow for load on the primary support mechanism.

20 Claims, 5 Drawing Sheets

SUPPORT STRUCTURE WITH RAISABLE COVER

BACKGROUND

The subject matter disclosed herein relates generally to support structures that include covers and, more particularly, safety and usability mechanisms for gantries and gantry covers. Support structures, including gantries, can be large and heavy systems. They may include a large number of components and parts. It is important to allow easy and safe ways to access these components and parts during service or adjustment of the systems.

Gantries are an important part of radiography and tomography systems. A medical imaging system can include a gantry comprising a stationary frame for supporting a rotor and attached components of the imaging chain. The rotor includes a central opening large enough to receive a patient extending along the scanning axis. The rotor is rotated about a patient during a scanning or imaging procedure. An x-ray tube can be positioned on the rotor diametrically across the central opening from an array of x-ray detectors. As the rotor rotates, the x-ray tube projects a beam of energy, or x-rays, along a scan plane, through a patient, and to the detector array. By rotating the x-ray source about the scanning axis and relative to the patient, x-rays are projected through a patient from many different directions. An image of the scanned portion of a patient can be constructed from data provided by the detector array using a computer.

Covers may be placed on the various sides of a support structure, including gantry, for improving the look, safety, and usability of the system. Allowing the easy manipulation of the covers for improved access to internal components of the support structure is a priority. Thus, improved systems for allowing easy manipulation of covers are proposed.

BRIEF DESCRIPTION

In accordance with an embodiment, a system is provided that includes a support structure; a cover for a side of the support structure; at least one hinge attached to the support structure and cover to allow the cover pivotal movement with respect to the support structure; wherein the hinge allows for an open position such that the cover does not cover a majority of the side of the support structure and a closed position such that the cover does cover a majority of the side of the support structure; at least one primary support mechanism attached to the hinge and support structure to support the weight of the cover when it is open position; and at least one additional support mechanism attached to the hinge to hold the cover in an open position. Further the pivotal movement can be a raising up and lowering down of the cover with respect to the support structure; and the primary support mechanism can provide force to raise the cover. Further, the cover may extend substantially horizontally outward from the top of the support structure in the open position.

In accordance with an embodiment the primary support mechanism may be a spring. In accordance with an embodiment the primary support mechanism is a gas spring, the gas spring further comprising: a first spring end attached to the hinge; a second spring end with a slot for an attachment mechanism to the support structure, wherein the slot allows for the attachment mechanism to the support structure to be at multiple positions; and a spring body attached to first spring end and second spring end.

In accordance with an embodiment the additional support mechanism may be a latch mechanism. In accordance with an embodiment the additional support mechanism may be a spring pin. The additional support mechanism can automatically engage with an aligned slot in the support structure when the cover reaches a first predetermined position in an opening operation. Further, the primary attachment mechanism can provide force to support the weight of the cover when the additional support mechanism is engaged with the aligned slot in the support structure at the first predetermined position. The system can include a release cable attached at one end to the additional support mechanism, running along the cover, and attached at the opposing end to a release lever, a release handle, or a release button.

The hinge can allow for an install position such that the cover is opened further than the open position and the additional support mechanism engages with the support structure at a second predetermined position. In some embodiments, the primary attachment mechanism provides no force to support the weight of the cover when the additional support mechanism is engaged with the support structure at the second predetermined position.

In accordance with an embodiment a gantry is provided that includes a stationary structure; a cover for a side of the stationary structure; at least two hinges, each hinge attached to the stationary structure and cover to allow the cover pivotal movement with respect to the stationary structure; wherein the hinges in combination allow for an open position such that the cover does not cover a majority of the side of the stationary structure and a closed position such that the cover does cover a majority of the side of the stationary structure; at least two gas springs, each gas spring attached to one hinge and the stationary structure to support the weight of the cover when it is open position; and at least two spring pins attached to the hinge to hold the cover in an open position; wherein the spring pins automatically engage with a receptacle in the stationary structure when the cover reaches a first predetermined position. The pivotal movement can be a raising up and lowering down of the cover with respect to the stationary structure; and the gas springs provide force to raise the cover. The cover can extend horizontally outward from the top of the stationary structure in the open position.

The gantry can further include a rotor; an x-ray source and an x-ray detector attached to the rotor; wherein the x-ray source emits x-rays toward a subject and the x-ray detector receives x-rays attenuated by the subject and sends out detected image data; and an image reconstructor that receives detected image data from the x-ray detector and reconstructs the image data into output images for display on an operator console.

The hinges allows for an install position such that the cover is opened further than the open position and the spring pins engage with the stationary structure at a second predetermined position, wherein the gas springs provide no force to support the weight of the cover when the spring pins are engaged with the stationary structure at the second predetermined position.

In some embodiments, each gas spring can include a first spring end attached to a hinge; a spring body; a spring rod; a second spring end with a slot for an attachment mechanism to the stationary structure, wherein the slot allows for the attachment mechanism to the stationary structure to be at multiple positions.

DETAILED DESCRIPTION

Figure 1:
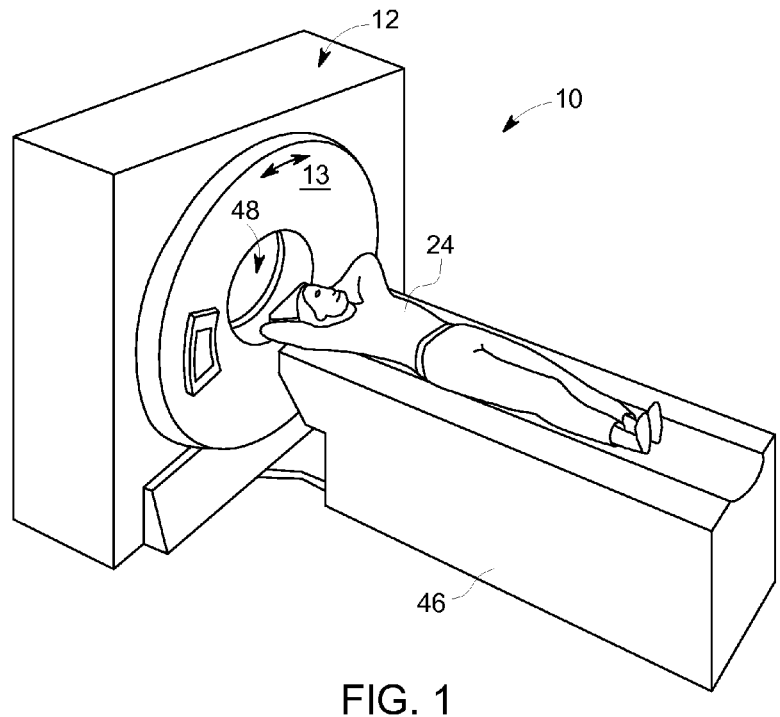
FIG. 1 is an angled view of an imaging system with a gantry in accordance with an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

A support structure, which may be an imaging system gantry, is disclosed. The support structure has at least one cover installed to cover a side of the support structure. The cover is raised pivotally by a primary support mechanism. The cover may be secured in place by an additional support mechanism. The additional support mechanism may be set in two different positions, one that allows for load on the primary support mechanism and another that does not allow for load on the primary support mechanism. One support structure embodiment is a gantry. Additional support structures can be other storage or mechanical systems that provide support for internal components and/or parts and have covers that may require opening. Examples may include sheet metal brackets, weldments, castings, or the like. The support structure may also be called a stationary structure.

Figure 2:
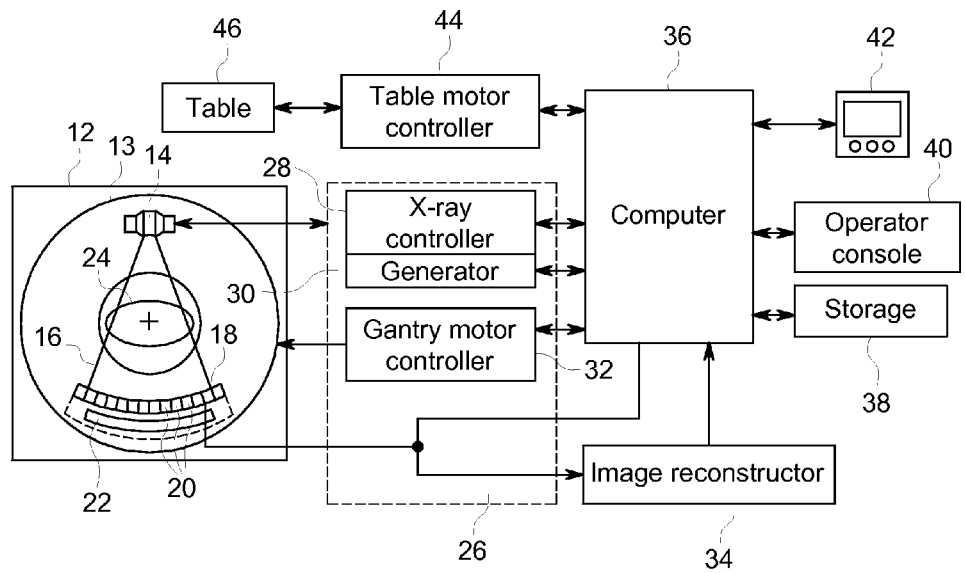
FIG. 2 is a block schematic diagram of an imaging system in accordance with an embodiment.

FIGS. 1 and 2 show a computed tomography (CT) imaging system 10 including a gantry 12. Gantry 12 has a rotor 13 an x-ray source 14 that projects a beam of x-rays 16 toward a detector assembly 18 on the opposite side of the rotor 13. A main bearing may be utilized to attach the rotor 13 to the stationary structure of the gantry 12. X-ray source 14 includes either a stationary target or a rotating target. Detector assembly 18 is formed by a plurality of detectors 20 and data acquisition systems (DAS) 22, and can include a collimator. The plurality of detectors 20 sense the projected x-rays that pass through a subject 24, and DAS 22 converts the data to digital signals for subsequent processing. Each detector 20 produces an analog or digital electrical signal that represents the intensity of an impinging x-ray beam and hence the attenuated beam as it passes through subject 24. During a scan to acquire x-ray projection data, rotor 13 and the components mounted thereon can rotate about a center of rotation.

Rotation of rotor 13 and the operation of x-ray source 14 are governed by a control mechanism 26 of CT system 10. Control mechanism 26 can include an x-ray controller 28 and generator 30 that provides power and timing signals to x-ray source 14 and a gantry motor controller 32 that controls the rotational speed and position of rotor 13. An image reconstructor 34 receives sampled and digitized x-ray data from DAS 22 and performs high speed image reconstruction. The reconstructed image is output to a computer 36 which stores the image in a computer storage device 38.

Computer 36 also receives commands and scanning parameters from an operator via operator console 40 that has some form of operator interface, such as a keyboard, mouse, touch sensitive controller, voice activated controller, or any other suitable input apparatus. Display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position subject 24 and gantry 12. Particularly, table 46 moves a subject 24 through a gantry opening 48, or bore, in whole or in part.

Figure 3:
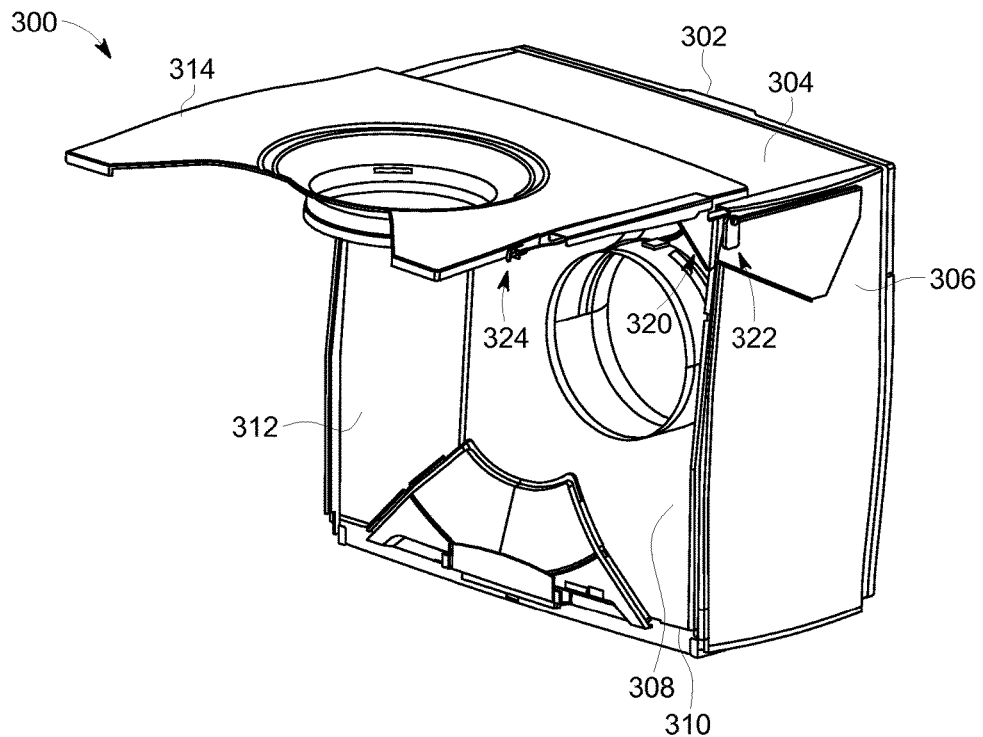
FIG. 3 is a perspective view of a gantry with a raised front cover in accordance with an embodiment.

FIG. 3 is a perspective view of a gantry with a raised front cover in accordance with an embodiment. Support system 300 includes a gantry 302 with a top cover 304, right side cover 306, back side cover 308, bottom side cover 310, left side cover 312, and front side cover 314. Gantry 302 is a support structure that includes covers on all six sides. Underneath the covers are the internal components of the system which may needed to be accessed at times for service, upgrade, adjustment, and other reasons. The embodiments herein discuss a single cover being raised, lowered, and being held in position, but a plurality of moveable covers attached to a single support structure can be implemented.

In the embodiment of FIG. 3, the front side cover 314 is attached to gantry 302 through a hinge 320. A second hinge may be implemented, one in each upper corner of the support structure in some embodiments, to provide balanced support to the cover. Support system 300 specifically includes a hinge 320, a side support plate 322, and cable release 324 at the attachment point between the front cover 314 and gantry 302. Hinge 320 may also be referred to as a pivot mechanism or a hinge plate. Hinge 320 is attached to both the front side cover 314, shown in an open position in FIG. 3, and gantry 302. The attachment implementations of front side cover 314 and gantry 320 may be directly to the structure of each, or through additionally attached support plates, such as support plate 322. Cable release 324 will be discussed further in reference to FIG. 5.

Figure 4:
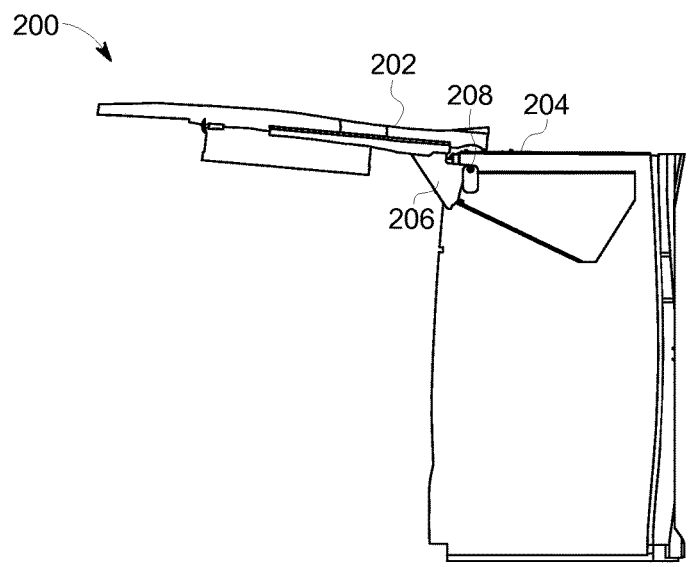
FIG. 4 is a side view of a support structure with a raised side cover in accordance with an embodiment

FIG. 4 is a side view of a support structure with a raised side cover in accordance with an embodiment. Support system 200 includes support structure 204, cover 202, hinge 206, and pivot point 208. Cover 202 is attached to support structure 204 through hinge 206. Hinge 206 is primarily attached to support structure 204 through pivot point 208. Pivot point 208 allows for pivotal motion of the front cover. Cover 202 can be raised as shown in FIG. 4 and lowered to where cover 202 is parallel to back cover, in a pivotal motion.

Figure 5:
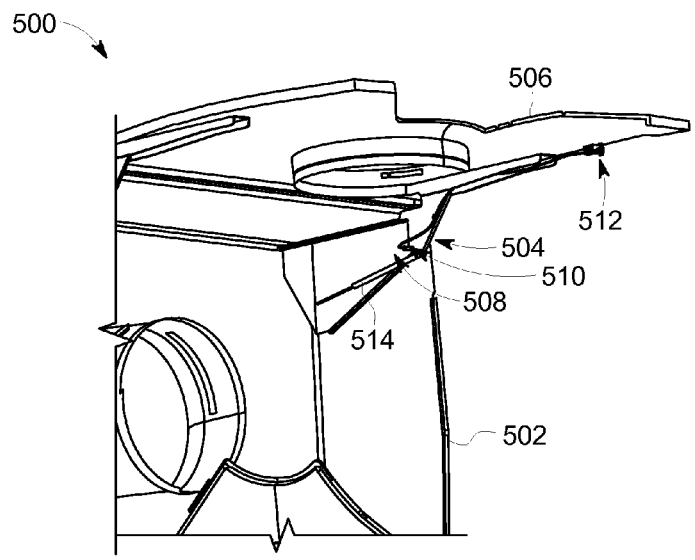
FIG. 5 is a zoomed perspective view of a gantry with a raised front cover in accordance with an embodiment.

FIG. 5 is a zoomed perspective view of a gantry with a raised front cover in accordance with an embodiment. Support system 500 includes a gantry 502, a hinge 504, a cover 506, a support plate 508, a spring pin 510, a cable release 512, and a spring 514. Support system 500 is shown in an open position in FIG. 5.

Gantry 502 is a support structure with cover 506 attached thereto through hinge 504. Hinge 504 moves in a pivotal motion during the raising and lowering process.

Spring 514 is attached to gantry 502 and hinge 504. Spring 514 provides force to hinge 504 to provide a pivotal lifting motion to cover 506. Spring 514 is a primary support mechanism. Spring 514 raises cover 506 and supports the weight of cover 506 when it is in an open position. Spring 514 can be a gas spring in an embodiment, or a coil spring, mechanical spring, hydraulic ram, pressurized fluids, torsional spring, counter weight in alternate embodiments. Spring 514 may also be referred to as a stored energy device.

Spring pin 510 is an automatically engaging additional support mechanism. Spring pin 510 is located near the pivot point of hinge 504 so as to minimize the footprint of hinge 504, in an embodiment. Spring pin 510 is attached to hinge 504 and extends into a pin receptacle in hinge 504. Pin receptacle may be a hole, slot, or recess in various embodiments. When cover 506 has reached a predetermined height of elevation, spring pin 510 and pin receptacle align with support receptacle and spring pin 510 automatically engages the support receptacle. Support receptacle may be a hole, slot, or other fitting in the support structure. Spring pin 510 is forced by its spring to extend the pin through the pin receptacle into the support receptacle so that spring pin 510 is fixed into place. No user action engaging the pin is necessary as the pin will automatically engage when the pin receptacle and support receptacle align. The spring pin may be an alternative latch mechanism in alternate embodiments.

Spring pin 510 is an additional support mechanism that may be considered a failsafe apparatus according to some embodiments. When engaged in the support receptacle, spring pin 510 prevents pivotal movement of the hinge, thus preventing the cover from further extending upward or retracting downward. Spring pin 510 thus holds the cover in an open position when it is engaged.

Cable release 512 is actuated by a user. Thus, cover 506 only lowers when a user specifically initiates a lowering operation in an embodiment. Cable release 512 is attached to cover 506 such that a user does not have to stand under the raised cover 506 in order to access cable release 512. FIG. 5 shows a cable running from cable release 512 to spring pin 510. The cable may be a sheathed cable. Activating cable release disengages the spring pin mechanism. This may be by pulling back spring pin 510 from within the support receptacle, thus allowing hinge to move pivotally again. Cable release 512 is shown as a t-shaped handle in FIG. 5. Cable release 512 may be implemented as a round handle, a disengage button, a lever, or other implementations in various embodiments. Further, cable release could be electronically controlled remotely by software on a device sending instructions to the gantry to release the spring pin 510 in alternate embodiments. Since the cable release 512 is located at the opposite end of the cover from hinge 504 in an embodiment, there exists a mechanical advantage relative to the spring 514 for a user to raise and/or lower the cover with minimal effort.

Support system 500 may include two hinges 504, two springs 514, two cable releases 512, two spring pins 510, and two support plates 508 for supporting the right and left sides of cover 506. During an event where the cover 506 needs to be open, such as a field service event, cover 506 is opened. During opening and once open, the weight of cover 506 is supported by the springs 514, which can be gas springs. Once open, the two spring pins 510 automatically engage by inserting into support receptacles in the support plates 508, holding cover 506 open until cover 506 is to be closed. Even if a spring 514 may suffer an issue supplying the necessary force, the engaged spring pin 510 would prevent lowering of cover 506. The user can then use the cable releases 512 for disengaging the spring pins 510 to allow for lowering of cover 506 to closed position.

Figure 10:
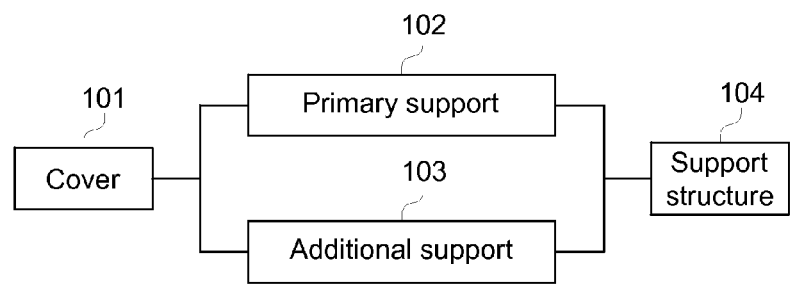
FIG. 10 is a block diagram of a first mode in accordance with an embodiment.

FIG. 10 details a first mode. FIG. 10 is a block diagram of a first mode in accordance with an embodiment. The first mode is a mode where the primary support mechanism, such as spring 514, spring 610, or primary support 102 bears the load and weight of a cover 101. Both the primary support 102 and additional support 103 engage with the support structure 104 and the cover 101.

Figure 11:
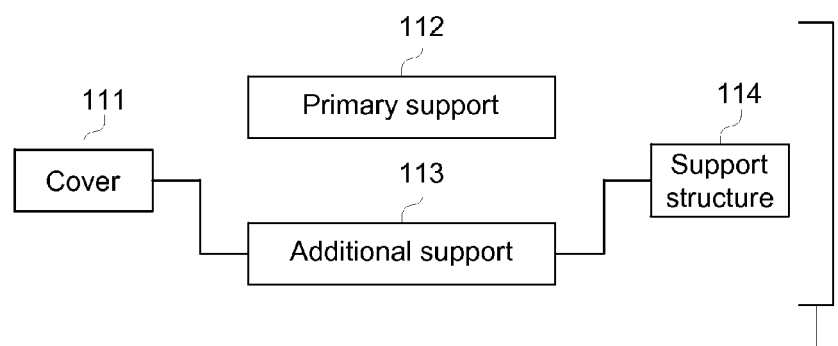
FIG. 11 is a block diagram of a second mode in accordance with an embodiment.

FIG. 11 details a second mode. FIG. 11 is a block diagram of a second mode in accordance with an embodiment. The second mode is where the primary support mechanism, such as spring 514, spring 610, or primary support 112 no longer bears the weight of a cover 111. Only the additional support 113 engages with the support structure 114 and cover 111 to hold cover 111 in an open position.

Figure 6:
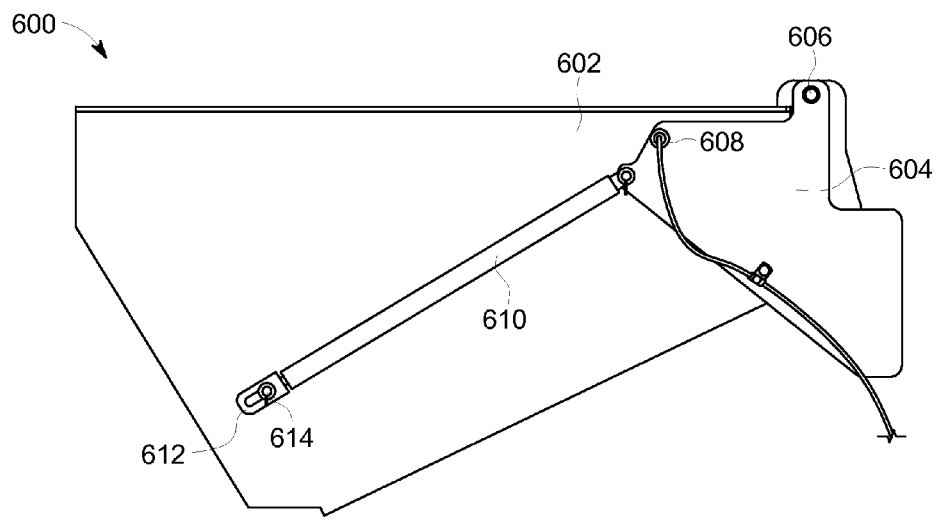
FIG. 6 is a side view of a primary support mechanism and a hinge in a first mode in accordance with an embodiment.

The first mode will now be discussed with reference to FIG. 6, FIG. 8, and FIG. 10. FIG. 6 is a side view of a primary support mechanism and a hinge in a first mode in accordance with an embodiment. FIG. 6 shows the system in a closed cover configuration. Support system 600 includes gantry 602, hinge 604, pivot point 606, spring pin 608, spring 610, spring end 612, and spring attachment mechanism 614. Spring pin 608 is not engaged with a support receptacle as it is not in the predetermined position. Thus, spring pin 608 is idle in a closed cover configuration.

Spring 610 is not providing lift in the closed configuration of FIG. 6, as the cover is closed and latched. Spring 610 is fully compressed as the cover is closed, thus its spring rod is almost fully within the spring body. The spring can the cover closed at this position, in at least one embodiment. Spring attachment mechanism 614 attaches spring 610 to gantry 602. FIG. 6 shows that spring end 612 has an opening large enough to allow spring end 612 to move in relation to spring attachment mechanism 614, from an engaged position, such as in FIG. 6, to a disengaged position, discussed further in relation to FIG. 7.

Figure 8:
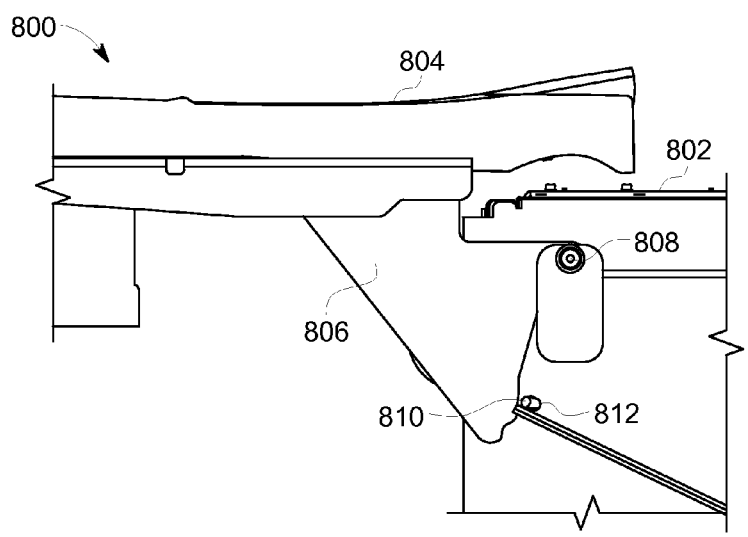
FIG. 8 is a side view of an additional support mechanism and hinge in a first mode in accordance with an embodiment.

FIG. 8 is a side view of an additional support mechanism and hinge in a first mode in accordance with an embodiment. FIG. 8 shows a system in an open cover configuration. This may be referred to as service position, as a service technician can now have access to the interior of the system for service activities. Support system 800 includes gantry 802, cover 804, hinge 806, pivot point 808, spring pin 810, and support receptacle 812. FIG. 8 shows hinge 806 implemented as a hinge plate having forced edge with no gaps between the hinge and support structure or cover so as to prevent pinch points, thus increasing safety.

Spring pin 810 has reached a predetermined position and thus has engaged and extended into support receptacle 812. Support receptacle 812, which may be a hole or slot in some embodiments, is shown as a bit larger than the diameter of spring pin 810. This allows for a bit of flexibility so as to allow spring pin 810 to move a bit related to the tolerance of the primary support mechanism. In an alternate embodiment, support receptacle 812 is substantially the same size as spring pin 810. Spring pin 810, as extended into support receptacle 812, prevents the movement of the cover in both the further open or further closed directions. It is an additional support mechanism that holds the cover in an open position.

Figure 7:
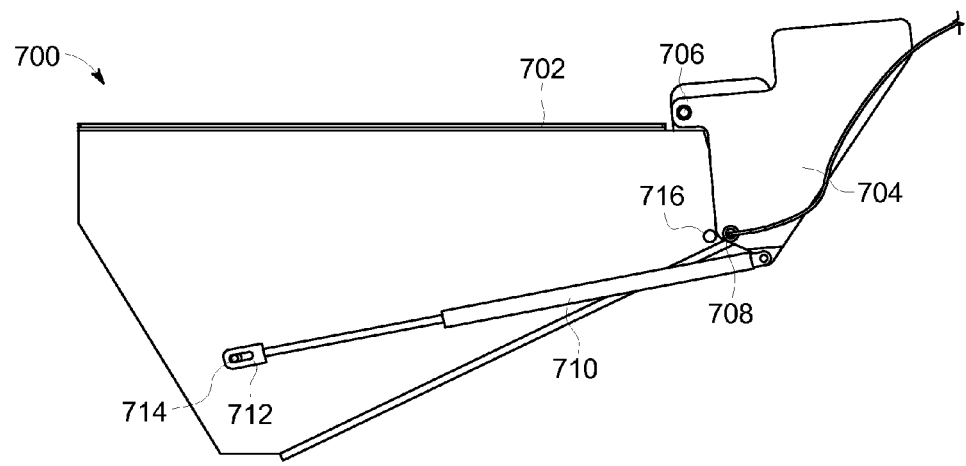
FIG. 7 is a side view of a primary support mechanism and a hinge in a second mode in accordance with an embodiment.
Figure 9:
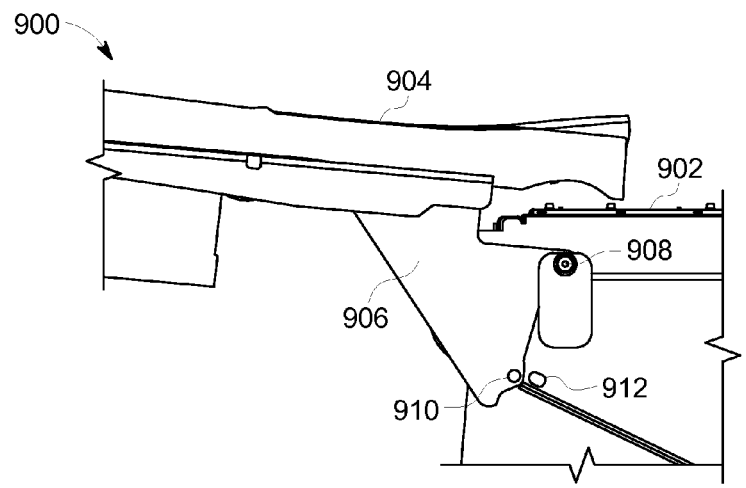
FIG. 9 is a side view of an additional support mechanism and hinge in a second mode in accordance with an embodiment.

The second mode will now be discussed with reference to FIG. 7, FIG. 9, and FIG. 11. FIG. 7 is a side view of a primary support mechanism and a hinge in a second mode in accordance with an embodiment. FIG. 9 is a side view of an additional support mechanism and hinge in a second mode in accordance with an embodiment.

FIG. 9 shows a system with an open cover in a second mode. Support system 900 includes gantry 902, cover 904, hinge 906, pivot point 908, spring pin 910, and support receptacle 912. FIG. 9 is similar to FIG. 8, except that spring pin 910 is at a second predetermined position, wherein the cover is extended more towards the open position. Support receptacle 912 is empty as the second predetermined position is further towards the support structure edge from support receptacle 912. At the second predetermined position there may be an edge, as is shown in FIG. 9, or a second support receptacle. FIG. 9 shows hinge 906 implemented as a hinge plate having forced edge with no gaps between the hinge and support structure or cover so as to prevent pinch points, thus increasing safety. Thus, in both modes, the specific hinge design prevents pinch points.

The second mode is to hold the cover in place during a service or exchange of the primary support mechanism. Thus, primary support mechanism is not providing any force in the second mode. FIG. 7 shows this. Support system 700 includes gantry 702, hinge 704, pivot point 706, spring pin 708, spring 710 as the primary attachment mechanism, spring end 712, spring attachment mechanism 714, and support receptacle 716.

Spring attachment mechanism 714 is shown as at the opposite end of spring end 712 from FIG. 6 as spring 710 has been extended past its force length. This is accomplished through the improved design of spring end 712 with an extended slot opening to allow for spring attachment mechanism 714 to travel to different locations within spring end 712. Thus, spring 710 is not placing any pressure on spring attachment mechanism 714 and is applying substantially no force to hinge 704. This spring end 712 design allows for cover pivotal movement beyond the stroke of the spring.

In this second mode, spring pin 708, as engaged with the gantry at the second predetermined position, holds a cover in an open position. This may be called an install position as it allows a service technician to remove an old spring and install a new spring as primary support mechanism without risk of the cover lowering or compression on the springs. The springs may be gas springs in an embodiment.

The embodiments herein describe improved ways to access the internal components of a support structure. This allows for fewer service personnel for particular system service operations. This allows also for faster and safer access to such a system.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A system, comprising: a support structure;
   a cover for a side of the support structure;
   at least one hinge directly attached to both the support structure and cover to allow the cover pivotal movement with respect to the support structure; wherein the hinge allows for an open position such that the cover does not cover a majority of the side of the support structure and a closed position such that the cover does cover a majority of the side of the support structure;
   at least one primary support mechanism directly attached to and extending from the hinge and attached to the support structure to support the weight of the cover when it is open position; and
   at least one additional support mechanism directly attached to and extending from the hinge to hold the cover in an open position.

2. The system of claim 1, wherein:
   the pivotal movement is a raising up and lowering down of the cover with respect to the support structure; and
   the primary support mechanism provides force to raise the cover.

3. The system of claim 1, wherein:
the cover extends substantially horizontally outward from the top of the support structure in the open position.

4. The system of claim 1, wherein:
the primary support mechanism is a spring.

5. The system of claim 1, wherein:
the additional support mechanism is a latch mechanism.

6. The system of claim 1, wherein:
the additional support mechanism is a spring pin.

7. The system of claim 1, wherein:
the additional support mechanism automatically engages with an aligned slot in the support structure when the cover reaches a first predetermined position in an opening operation.

8. The system of claim 7, wherein:
the primary attachment mechanism provides force to support the weight of the cover when the additional support mechanism is engaged with the aligned slot in the support structure at the first predetermined position.

9. The system of claim 1, wherein:
the hinge allows for an install position such that the cover is opened further than the open position and the additional support mechanism engages with the support structure at a second predetermined position.

10. The system of claim 9, wherein:
the primary attachment mechanism provides no force to support the weight of the cover when the additional support mechanism is engaged with the support structure at the second predetermined position.

11. The system of claim 1, further comprising:
a release cable attached at one end to the additional support mechanism, running along the cover, and attached at the opposing end to a release lever, a release handle, or a release button.

12. The system of claim 1, wherein:
the primary support mechanism is a gas spring, the gas spring further comprising:
a first spring end directly attached to the hinge;
a second spring end with a slot for an attachment mechanism to the support structure, wherein the slot allows for the attachment mechanism to the support structure to be at multiple positions; and
a spring body attached to first spring end and second spring end.

13. A gantry, comprising:
a stationary structure;
a cover for a side of the stationary structure;
at least two hinges, each hinge directly attached to both the stationary structure and cover to allow the cover pivotal movement with respect to the stationary structure; wherein the hinges in combination allow for an open position such that the cover does not cover a majority of the side of the stationary structure and a closed position such that the cover does cover a majority of the side of the stationary structure;
at least two gas springs, each gas spring directly attached to and extending from one hinge and attached to the stationary structure to support the weight of the cover when it is open position; and
at least two spring pins, each spring pin is directly attached to and extends from one hinge to hold the cover in an open position; wherein the spring pins automatically engage with a receptacle in the stationary structure when the cover reaches a first predetermined position.

14. The gantry of claim 13, wherein:
the pivotal movement is a raising up and lowering down of the cover with respect to the stationary structure; and
the gas springs provide force to raise the cover.

15. The gantry of claim 13, wherein:
the cover extends horizontally outward from the top of the stationary structure in the open position.

16. The gantry of claim 13, wherein:
the hinges allows for an install position such that the cover is opened further than the open position and the spring pins engage with the stationary structure at a second predetermined position.

17. The gantry of claim 16, wherein:
the gas springs provide no force to support the weight of the cover when the spring pins are engaged with the stationary structure at the second predetermined position.

18. The gantry of claim 13, further comprising:
at least one release cable attached at one end of a spring spin, running along the cover, and attached at the opposing end to a release lever, a release handle, or a release button.

19. The gantry of claim 13, wherein each gas spring further comprises:
a first spring end directly attached to a hinge;
a spring body;
a spring rod;
a second spring end with a slot for an attachment mechanism to the stationary structure, wherein the slot allows for the attachment mechanism to the stationary structure to be at multiple positions.

20. The gantry of claim 13, further comprising:
a rotor;
an x-ray source and an x-ray detector attached to the rotor; wherein the x-ray source emits x-rays toward a subject and the x-ray detector receives x-rays attenuated by the subject and sends out detected image data; and
an image reconstructor that receives detected image data from the x-ray detector and reconstructs the image data into output images for display on an operator console.

* * * * *